US010987032B2

(12) United States Patent
Ambrósio

(10) Patent No.: US 10,987,032 B2
(45) Date of Patent: Apr. 27, 2021

(54) METHOD, SYSTEM, AND APPARATUS FOR REMOTELY CONTROLLING AND MONITORING AN ELECTRONIC DEVICE

(71) Applicant: Cláudio Afonso Ambrósio, Muriae-Minas Gerais (BR)

(72) Inventor: Cláudio Afonso Ambrósio, Muriae-Minas Gerais (BR)

(*) Notice: Subject to any disclaimer, the term of this patent is extended or adjusted under 35 U.S.C. 154(b) by 234 days.

(21) Appl. No.: 15/285,774

(22) Filed: Oct. 5, 2016

(65) Prior Publication Data
US 2018/0092576 A1    Apr. 5, 2018

(51) Int. Cl.
*A61B 5/145* (2006.01)
*H04W 4/02* (2018.01)
(Continued)

(52) U.S. Cl.
CPC ........ *A61B 5/14532* (2013.01); *A61B 5/0002* (2013.01); *A61B 5/0004* (2013.01); *A61B 5/0205* (2013.01); *A61B 5/6801* (2013.01); *A61B 5/746* (2013.01); *A61B 5/7465* (2013.01); *A61M 5/14244* (2013.01); *G16H 10/60* (2018.01); *G16H 10/65* (2018.01); *G16H 20/17* (2018.01); *G16H 40/67* (2018.01); *G16H 50/70* (2018.01); *G16H 80/00* (2018.01); *H04L 67/12* (2013.01); *H04L 67/125* (2013.01); *H04W 4/02* (2013.01); *H04W 4/029* (2018.02); *A61M 2005/14208* (2013.01)

(58) Field of Classification Search
CPC ......... A61B 5/024; A61B 5/08; A61B 5/0002; A61B 5/0008; A61B 5/14532; A61B 5/6801; A61M 2005/14208; A61M 5/14244; G06F 19/00; G06F 19/3468; G16H 10/65; H04L 65/403; H04L 67/12; H04W 4/02
See application file for complete search history.

(56) References Cited

U.S. PATENT DOCUMENTS

| 5,558,640 A * | 9/1996 | Pfeiler ............... A61M 5/14276 604/67 |
| 6,589,169 B1 * | 7/2003 | Surwit ................... G16H 50/20 600/300 |

(Continued)

*Primary Examiner* — Quynh-Nhu H. Vu
(74) *Attorney, Agent, or Firm* — Wenderoth, Lind & Ponack, L.L.P.

(57) ABSTRACT

In one embodiment, a system, method, and apparatus are provided which enable remote monitoring and control of a patient's wearable medical device. The wearable medical device may collect bodily data that characterizes their condition and transmits such data to an electronic device viewable by a remote party such as a physician, close family member or friend, or other party communicatively linked in a treatment network. Considering the transmitted bodily data relative to predetermined threshold conditions as a guide, the remote party may cause the wearable electronic device to dispense therapeutic treatments into the patient's body in an effort to immediately facilitate treatment of the patient's condition regardless of geographic proximity. The wearable medical device may be also configured to automatically transmit alerts to electronic devices of remote parties, triggering treatment and other forms of aid in the event of an emergency.

12 Claims, 6 Drawing Sheets

(51) Int. Cl.

| | | |
|---|---|---|
| *H04L 29/08* | (2006.01) | |
| *H04L 29/06* | (2006.01) | |
| *A61B 5/00* | (2006.01) | |
| *A61B 5/024* | (2006.01) | |
| *A61B 5/08* | (2006.01) | |
| *A61M 5/142* | (2006.01) | |
| *H04W 4/029* | (2018.01) | |
| *G16H 10/60* | (2018.01) | |
| *A61B 5/0205* | (2006.01) | |
| *G16H 80/00* | (2018.01) | |
| *G16H 20/17* | (2018.01) | |
| *G16H 50/70* | (2018.01) | |
| *G16H 40/67* | (2018.01) | |
| *G16H 10/65* | (2018.01) | |

(56) References Cited

U.S. PATENT DOCUMENTS

| | | | | |
|---|---|---|---|---|
| 2003/0060765 A1* | 3/2003 | Campbell | | G16H 40/63 604/131 |
| 2004/0078220 A1* | 4/2004 | Jackson | | G16H 40/20 705/2 |
| 2007/0185736 A1* | 8/2007 | Cervi | | G16H 20/10 705/2 |
| 2009/0088088 A1* | 4/2009 | Caswell | | G06F 13/387 455/90.1 |
| 2011/0082711 A1* | 4/2011 | Poeze | | A61B 5/14532 705/3 |
| 2011/0320130 A1* | 12/2011 | Valdes | | A61B 5/7278 702/19 |
| 2012/0108991 A1* | 5/2012 | Song | | A61B 5/1118 600/509 |
| 2012/0154157 A1* | 6/2012 | George | | G08B 21/02 340/584 |
| 2012/0189140 A1* | 7/2012 | Hughes | | H04M 3/56 381/123 |
| 2012/0191061 A1* | 7/2012 | Yodfat | | A61M 5/1413 604/503 |
| 2012/0238853 A1* | 9/2012 | Arefieg | | A61B 5/150412 600/365 |
| 2014/0180203 A1* | 6/2014 | Budiman | | A61B 5/14532 604/66 |
| 2014/0278552 A1* | 9/2014 | Hold | | G16H 20/10 705/3 |
| 2015/0073393 A1* | 3/2015 | Moberg | | G16H 40/67 604/890.1 |
| 2016/0113565 A1* | 4/2016 | Lee | | A61B 5/02055 701/533 |
| 2016/0210429 A1* | 7/2016 | Ortiz | | G16H 10/60 |
| 2016/0263317 A1* | 9/2016 | Arefieg | | A61B 5/4839 |
| 2017/0076052 A1* | 3/2017 | Phillips | | G06Q 10/06311 |
| 2017/0200050 A1* | 7/2017 | Zhang | | G06F 16/739 |

* cited by examiner

METHOD, SYSTEM, AND APPARATUS FOR REMOTELY CONTROLLING AND MONITORING AN ELECTRONIC DEVICE

CROSS-REFERENCE TO RELATED APPLICATIONS

Pursuant to 35 USC 119, this application claims the right of priority to Provisional Patent Application Ser. No. 62/237,183 filed on Oct. 5, 2015. The content of said application is incorporated herein by reference in its entirety.

GOVERNMENT CONTRACT

Not applicable.

STATEMENT RE. FEDERALLY SPONSORED RESEARCH/DEVELOPMENT

Not applicable.

COPYRIGHT & TRADEMARK NOTICES

A portion of the disclosure of this patent document may contain material which is subject to copyright protection. This patent document may show and/or describe matter which is or may become trade dress of the owner. The copyright and trade dress owner has no objection to the facsimile reproduction by any one of the patent document or the patent disclosure, as it appears in the Patent and Trademark Office patent files or records, but otherwise reserves all copyrights and trade dress rights whatsoever.

TECHNICAL FIELD

The disclosed subject matter relates generally to electronic devices and, more particularly, to electronic devices configured to wirelessly communicate with and receive remote instructions to initiate operation from another remote electronic device.

BACKGROUND

Wearable drug delivery systems are known in the art for treating and managing chronic and/or terminal medical conditions. Such systems and apparatuses increase quality of life for patients who may otherwise be forced to focus their attention and energy on monitoring the state of their condition. For instance, it is well known that some conditions, such as diabetes, require patients to monitor their own blood glucose levels throughout the day and, in response to certain low or high measurements, consume or inject prescribed amounts of carbohydrates or alternatively inject prescribed amounts of insulin. Indeed, it is well known that the delivered volume of any of these treatments depends on the specific amount of sugar in the blood. Ensuring timely and effective delivery of a treatment is often dependent on various factors susceptible to daily or hourly fluctuation. As a result, patients often work closely with their physicians and even close acquaintances to manage their condition.

In spite of careful monitoring and management, the fluctuating nature of some conditions may result in imperfect or similarly fluctuating prescriptions. Unfortunately this issue is exacerbated by the fact that it is not always practical to convene with a doctor or other consultant who can personally address any changing needs.

As an example of the problem, hypoglycemia is a condition in which patients have abnormally low blood glucose levels. This often occurs in conjunction with glucose circulation conditions such as diabetes. Because symptoms of hypoglycemia—including nervousness, anxiety, impatience, irritability, confusion, physical weakness, fatigue, and even unconsciousness—are usually present in a patient after the patient's blood glucose levels have already fallen well below healthy levels, patients are often unable to tell in advance when they are going to experience a hypoglycemic episode. Thus patients are often rendered incapable of effectively caring for themselves, and fail to stop insulin delivery and/or begin delivering glucose to their body through the prescribed methods when the symptoms occur. This can be particularly problematic because untimely treated hypoglycemic episodes are known to have dire consequences. For example, symptoms such as dizziness and blurred and impaired vision have been known to cause traffic accidents when they occur while driving. In other instances, patients can experience hypoglycemic coma and even death if they fail to timely treat the condition with effective amounts of prescribed treatments. This can particularly dangerous in the event that a patient experiences unexpected changes to his or her condition and is unable to address it themselves, whether on account of the nature of their current treatment plan or incapacitation.

Some remotely controllable treatment devices have been proposed. For instance, U.S. Pat. No. 5,928,195 to Malamud et al. and U.S. Pat. No. 6,464,687 to Ishikawa et al. disclose varying implantable drug delivery systems However, these are deficient at least for failing to combine the ability to remotely monitor and affect dosage as well as facilitate delivery and treatment in the event of an emergency.

Although various proposals have been made to solve the problem, none of those in existence combine the characteristics of the present invention. Therefore, there is a need for a system, method, and apparatus that effectively increase the likelihood that a patient receives personalized and effective treatment for a condition and is further remotely treatable in the event that an emergency with respect to the condition develops.

SUMMARY

The present disclosure is directed to systems, methods, and apparatuses for electronically requesting therapeutic response from a remote location. More particularly, the disclosure is directed to an electronic device having an electronic control circuit configured to receive remote, wireless instructions from an electronic device, such a computer or cellphone, controlled by a remote party chosen from among a patient's personal contacts and/or caregivers. It is contemplated that the remote party may use their electronic device to, in some embodiments, communicate instructions causing the electronic control circuit housed in the medical device to optionally activate or deactivate such medical device, effectively treating the patient from a remote location. In some embodiments, the medical device may be configured to collect and wirelessly communicate various bodily data characterizing the patient's condition. The medical device may be operative to continuously, periodically, or even manually transmit such data to the personal electronic devices respective of each of one or more pre-selected remote parties.

For purposes of summarizing, certain aspects, advantages, and novel features have been described. It is to be understood that not all such advantages may be achieved in accordance with any one particular embodiment. Thus, the disclosed subject matter may be embodied or carried out in a manner that achieves or optimizes one advantage or group of advantages without achieving all advantages as may be taught or suggested.

In an embodiment, the medical device is an infusion pump, known to those skilled in the art. Such pumps wearable by a patient and known by those skilled in the art to deliver therapeutic doses of prescribed medication via a cannula inserted in the patient. Such pumps may be programmed to automatically deliver doses of prescribed medication into the body of the patient at regular intervals, deliver doses of prescribed medication upon electronically communicated receipt of information regarding threshold patient conditions, or even be manually instructed to deliver such dosages by the patient or caregiver. In accordance with one non-limiting embodiment then, for example, the medical device is any insulin pump such as those commonly prescribed for use by diabetic patients. In another embodiment, the medical device may be a glucose monitor also commonly prescribed to diabetic patients, or others having chronic metabolic conditions. In still other embodiments, the medical device is a combination of the two and may even further comprise a glucose or Glucagon pump. It is contemplated, though, and one skilled in the art will recognize, that the invention may be practiced with any of the aforementioned medical devices, a combination of the same, or any of those that may be developed as the field of electronic wearable medical devices continues to improve so long as it is capable of wireless communication with one or more personal electronic devices as discussed in further detail below.

It should be noted that in some embodiments, the electronic control circuit may be contained in a device other than an electronic wearable medical device. For instance, various household electronics, such as a television, air conditioning system, watering or sprinkler system, security system may be configured to receive remote, wireless instructions from a personal electronic device, such as a computer or cellphone. Thus one skilled in the art will recognize that the technology disclosed herein is not limited in applicability to the field of medical devices. Instead, a medical device is described for the sake of brevity and in the interest of enabling the technology only. As in the case of a medical device, then, is contemplated that a party in possession of a personal electronic device may use the device to, in some embodiments, communicate instructions causing an electronic control circuit housed in another device, such as another personal electronic device or even household electronic device, to optionally activate or deactivate the personal or household electronic device. In such embodiments, the personal or household device may be configured to wirelessly communicate various conditions, which may be continuously, periodically, or manually transmitted by the personal or household device to the personal electronic devices respective of each of one or more pre-selected party. For example, and without limitation, the personal or household devices may communicate whether such personal or household devices are powered on or off to one or more pre-selected parties' device.

Returning with particular attention paid to the example of an electronic wearable medical device, or simply "medical device" for the sake of brevity, the electronic control circuit of the medical device may be activated to deliver a therapeutic dose of a prescribed drug by instructions communicated via the one or more of the personal electronic devices. To ensure safe, effective, and timely dosage, the medical device may further be configured as a wireless data transmitter capable of communicating a patient's condition through various communication networks. For example, where the medical device comprises a blood glucose monitor and pump, the medical device may periodically report the patient's particular blood glucose levels to any personal electronic devices that have been communicatively linked to the medical device. Having received a report of the patient's condition along with a request from the patient for remote treatment, then, a remote party may use their electronic device, communicatively linked with the medical device, to transmit instructions activating the medical device.

It is contemplated that the medical device may be configured to be capable of communicatively linking wirelessly to various electronic devices via Wi-Fi, Bluetooth, cellular data or any other communication network available to read and carry out portable commands transmitted from such personal electronic devices. For example, in some embodiments, the medical device may communicate over digital cellular networks used by mobile phones such as GSM, cellular communication data services such as GPRS, and satellite systems such as GPS. Of course, those skilled in the art will recognize that various other communication networks that are currently available or may become available will be sufficient to practice the disclosure.

The one or more electronic devices wirelessly and communicatively linkable to the medical device may be chosen from any of a personal, laptop, or tablet computer; and land line or mobile telephone, cell phone, or smart phone. Indeed, it is contemplated that any desirable party may be granted access to communicate with the patient's medical device. For instance, the personal electronic device may include an application executed on the electronic device which communicatively links the device to the medical device. It is contemplated that such a communicative link may allow a remote party in possession of the linked electronic device to remotely control or otherwise transmit instructions effecting operation of the wearable medical device. So, for example, in the event that the medical device communicates a patient's request for treatment, to an electronic device, the user of such electronic device may use the electronic device to affirmatively transmit instructions remotely causing the control circuit in the medical device to activate and take corrective action, such as injecting a medication or stopping injection of a medication.

One skilled in the art will recognize that the remote party may be chosen from any emergency contacts or caregivers selected by a patient. For example, one remote party may be the patient's spouse, communicatively linked to the patient's medical device via a smart phone, laptop or home computer. Another remote party may be a primary care physician communicatively linked to the patient's medical device via a computer. Yet another remote party may be a friend or coworker of the patient communicatively linked to the patient's medical device via any of his or her own personal electronic devices such as a mobile phone or personal, laptop or tablet computer. Thus, neither the quantity of remote parties nor specific relationship to the patient is dispositive. Indeed, such remote parties may be chosen based on the particular needs of the patient owing consideration to, for example, the severity of the patient's condition, the particular need for immediate response to monitored conditions, the extent of possible injury as consequence of the patient's condition, and the patient's personal desire for additional independence and/or security.

As an example of the system in practice, in some embodiments, the medical device is a glucose monitor. The glucose monitor may report that a patient's blood glucose levels have fallen below healthy levels. In one embodiment, this may mean that the patient's glucose monitor measures blood glucose levels below 70 mg/dl. In some embodiments, the glucose monitor may be programmed to report levels that are unhealthy on an individualized basis. Thus, when low blood sugar is reported to a personal electronic device by a glucose monitor, a user in possession of the personal electronic device may remotely instruct the medical device to effect corrective action. In the case of hypoglycemia, or low blood sugar, corrective action may be causing any insulin delivery to stop. Corrective action may also be to automatically deliver glucose or Glucagon injections.

Thus, a remote party may aid treatment of a patient even when such party is geographically distanced from the patient. In the foregoing example, a patient wearing an insulin and/or glucose pump may be prevented from experiencing inconvenient or even life threatening hypo or hyperglycemic episodes as a remote party in possession of a communicatively linked electronic device is able to remotely command therapeutic treatment, such as by remotely instructing relevant medical devices to begin or end delivery of insulin or glucose to the patient as the case may be.

Of course the foregoing is offered by way of example only and not of limitation. It is contemplated that various medical devices may be remotely activated by or otherwise communicated with by the various personal electronic devices in the system. For example, the medical device may be an electronically controlled aerosol dispenser so that a remote electronic device may electronically transmit instructions that cause a dose to be emitted or altered in terms of timing or volume.

It is contemplated that the medical device may be even further operative to to transmit various data relating to a patient's condition, or bodily data, to the remote parties in possession of any communicatively linked electronic devices. For example, the medical device may be operative to transmit a patient's heart rate and temperature. In some embodiments, the medical device may even be configured to transmit the location of the patient to the electronic devices so that, if needed, aid may be efficiently dispatched or rendered in-person. In some embodiments, the medical device may be further operative to transmit any sounds in the vicinity of the patient. For example, a remote party may be able to assess the quality of a patient's breathing, that is whether it is unusually labored or shallow. One skilled in the art will recognize that that such exemplary and non-limiting features may aid remote parties having personal electronic devices in communication with the medical device in locating a possibly distressed patient as well as timely asserting diagnosis in case of medical distress or incapacitation.

Thus, it is an object of the invention to provide systems and methods for remotely turning on and off various medical devices.

It is another object of the invention to provide systems and methods for monitoring and remotely controlling various personal and household electronic devices.

It is another object of the invention to provide means for alerting remote parties to a patient's emergency condition.

It is still another object of the invention to transmit a patient's geographical location to a third party to aid location in the event of an emergency.

It is yet another object of the invention to transmit ambient sound from a patient and his or her surroundings to a third party to allow a remote party to judge the severity of a possible emergency even when such party cannot physically assess the patient's condition due to geographical proximity.

It is another object of the invention to avoid accidents and life threatening injuries from failure to receive timely and effective amounts of treatment.

It is an object of the invention to enable remote adjustment of drug dosages from health care professional in response to data monitored and reported by a medical device.

One or more of the above-disclosed embodiments, in addition to certain alternatives, are provided in further detail below with reference to the attached figures. The disclosed subject matter is not, however, limited to any particular embodiment disclosed.

Figure 1:
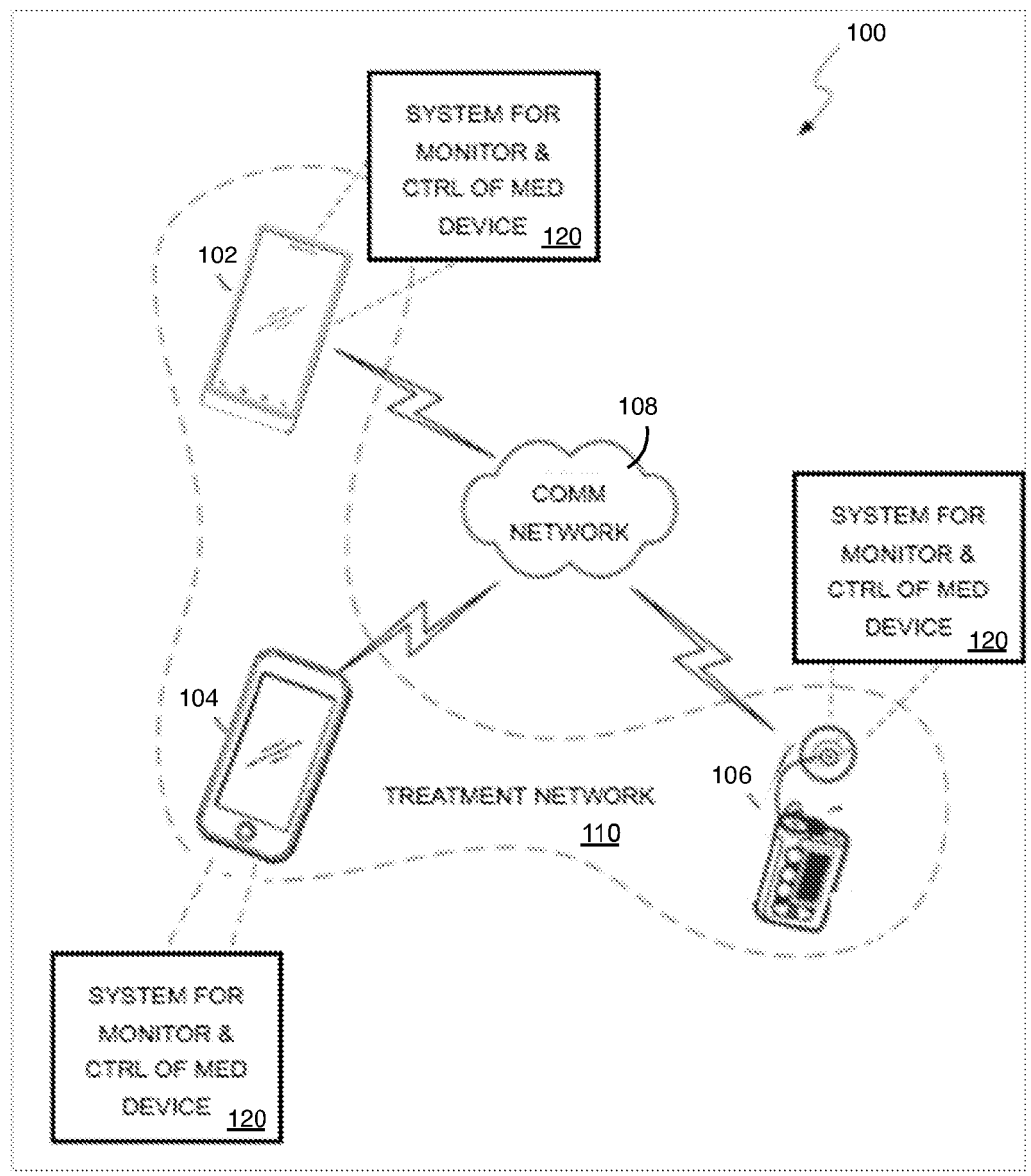
FIG. 1 is a block diagram of a networked environment in which an exemplary embodiment of a system for remotely monitoring and controlling an electronic device is implemented.

One embodiment of the invention is implemented as a program product for use with a computer system. The program(s) of the program product defines functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive) on which information is permanently stored; (ii) writable storage media (e.g., floppy disks within a diskette drive or hard-disk drive) on which alterable information is stored. Such computer-readable storage media, when carrying computer-readable instructions that direct the functions of the present invention, are embodiments of the present invention. Other media include communications media through which information is conveyed to a computer, such as through a computer or telephone network, including wireless communications networks. The latter embodiment specifically includes transmitting information to/from the Internet and other networks. Such communications media, when carrying computer-readable instructions that direct the functions of the present invention, are embodiments of the present invention. Broadly, computer-readable storage media and communications media may be referred to herein as computer-readable media.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-readable format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus The terms "couple," "coupled," "couples," "coupling," and the like should be broadly understood and refer to connecting two or more elements or signals, electrically, mechanically or otherwise. Two or more electrical elements may be electrically coupled, but not mechanically or otherwise coupled; two or more mechanical elements may be mechanically coupled, but not electrically or otherwise coupled; two or more electrical elements may be mechanically coupled, but not electrically or otherwise coupled. Coupling (whether mechanical, electrical, or otherwise) may be for any length of time, e.g., permanent or semi-permanent or only for an instant.

DETAILED DESCRIPTION

Having summarized various aspects of the present disclosure, reference will now be made in detail to that which is illustrated in the drawings. While the disclosure will be described in connection with these drawings, there is no intent to limit it to the embodiment or embodiments disclosed herein. Rather, the intent is to cover all alternatives, modifications and equivalents included within the spirit and scope of the disclosure as defined by the appended claims.

FIG. 1 is an illustrative embodiment of a networked environment in which an exemplary embodiment of a system for remotely controlling and monitoring an electronic device is implemented. The system 100 may comprise a plurality of electronic devices 102, 104 shown, for example only and not limitation, as mobile smart phones. It is contemplated, however, that the electronic devices may be any computing device operative to transmit and receive data over any of one or more various communication network types, including, for example cellular and Wi-Fi communications.

The system 100 further comprises an electronic device 106 such as an electronic wearable medical device. In an embodiment, the medical device 106 is operative to dispense therapeutic doses of certain prescribed treatments. For instance, one medical device 106 may be an insulin pump, a glucose or Glucagon pump, a combination of the two, or even a pump for other types of hormones. Such devices are known in the art and may comprise an electronic control circuit housed in the medical device to optionally activate or deactivate such medical device, effectively delivering a prescribed dose of treatment into the body of the patient. Activation of the electronic control circuit may occur when a patient presses a button on the housing, or on a remote control electronically communicating with the medical device. The device may even be programmed to regularly dispense dosages at a prescribed time.

The medical device 106 may be further operative to collect bodily data, such as any of blood glucose levels, heart rate, respiratory rate, and temperature. Thus, the aforementioned exemplary pumps may comprise monitors such as glucose monitors in communication with said pumps. It is contemplated, however, that a patient may alternatively manually collect bodily data, which may be digitally stored and transmitted via the system 100 to a remote party communicatively linked in the treatment network and still benefit from remote monitoring and control as disclosed.

It should be noted that in some embodiments, the electronic device 102, 104 may be communicatively linked to an intermediate electronic device such as a remote control, which is itself communicatively linked to the wearable medical device via Bluetooth, RFID and other proximity-dependent wireless and even wired systems, however, these are known in to those skilled in the art. Thus, for the sake of brevity, the elements will be discussed generally as the medical device. Likewise, one skilled in the art will recognize that it is not necessary that the invention be worn permanently to practice the invention. Many electronic wearable medical devices may be periodically removed, in fact, for charging and even for the patient's personal comfort.

Users of electronic devices 102, 104 and medical device 106 may create their own private treatment network 110 in which to monitor, and eventually diagnose and treat, the patient's condition.

In some embodiments, the network 110 enables members to use their users of electronic devices 102 and 104 to communicate with each other regarding the patient's condition. For instance, a parent may manage their child patient's treatment and use their electronic device, operative to receive bodily data from the child's medical device, to communicate the child's condition or to manually transmit additional data to the child's physician, in possession of another of the electronic devices so that the physician and parent are able to interact with each other regarding the child's treatment. As another example, a plurality of electronic devices may be in control of different medical specialists, each monitoring the patient's condition.

The treatment network 110 may be facilitated by a website or web-based application that may require a registration and login prior to use. Indeed, it is contemplated that owing to the sensitive nature of medical conditions and requirements for maintaining patient privacy, credentials and consent to join the network may be required. In the event that transmissions occur over a cellular network, rather than website or web-based application, it is contemplated that providing a predetermined code or even phone number may be sufficient to establish membership in the network. Regardless of how such a treatment network is implemented (be it web-based or not), the functionality of concern involves the ability to provide interaction among a limited group of members, as may be established by the members themselves.

In operation, the system 100 provides a better and more coordinated way of monitoring a patient's medical condition and remotely ensuring that he or she is able to receive proper treatment. Specifically, the system 100 enables a patient to transmit a request for treatment from their medical device 106 which may be received by any or one of the electronic devices in the treatment network 110. Upon receiving the request, a remote party using the electronic device 102, 104 may in turn transmit instructions causing the medical device 106 to dispense treatment. This may be further aided by the remote party's consideration for any bodily data which may have been collected and/or transmitted from the medical device 106 as well. For instance, a patient may recognize that their lightheadedness and rapid heartbeat, or other symptoms, may be an early sign of a hypoglycemic episode but be unsure of their ability to treat the condition with food or drink or prescribed tablets. The patient may then use their medical device 106 to request treatment. Bodily data, such as current or recent blood sugar levels, may in some embodiments be or have already been transmitted to other members, or remote parties, in the treatment network 110, and be used by a remote party to determine whether remote treatment is warranted. If it is, the remote party may send instructions to remotely activate the medical device 106 so that it may deliver a therapeutic dose of, in the exemplary case glucose or Glucagon, into the body of the patient. Confirmation may be transmitted by the medical device 106 to let the remote party know that remote treatment was successful. Confirmation may take place in one or two steps, or even more, such as via digital confirmation as a text message and also through prompting a phone call, though the exact method of confirmation is not dispositive.

Additionally, system 100 receives information corresponding to the location of the patient. In one embodiment, this information may be collected by a mobile device 102, 104 or 106 from integrated positioning technology, such as a Global Positioning System (GPS). However, it should be noted that various methods of determining the location of a mobile device can be used. This may be particularly desirous in cases where a patient's condition may result in unconsciousness or other incapacitation. Similarly, the medical device 106 may be operative to transmit ambient sounds to remote parties in the treatment network 110. This may allow a patient to describe or otherwise automatically transmit audible evidence of their location and symptoms in real time.

In this regard, electronic devices 102, 104, and medical device 106 include a patient monitoring and treatment system 100, which can be implemented in numerous ways such as, for example and without limitation, an application executed on an electronic device.

Figure 2:
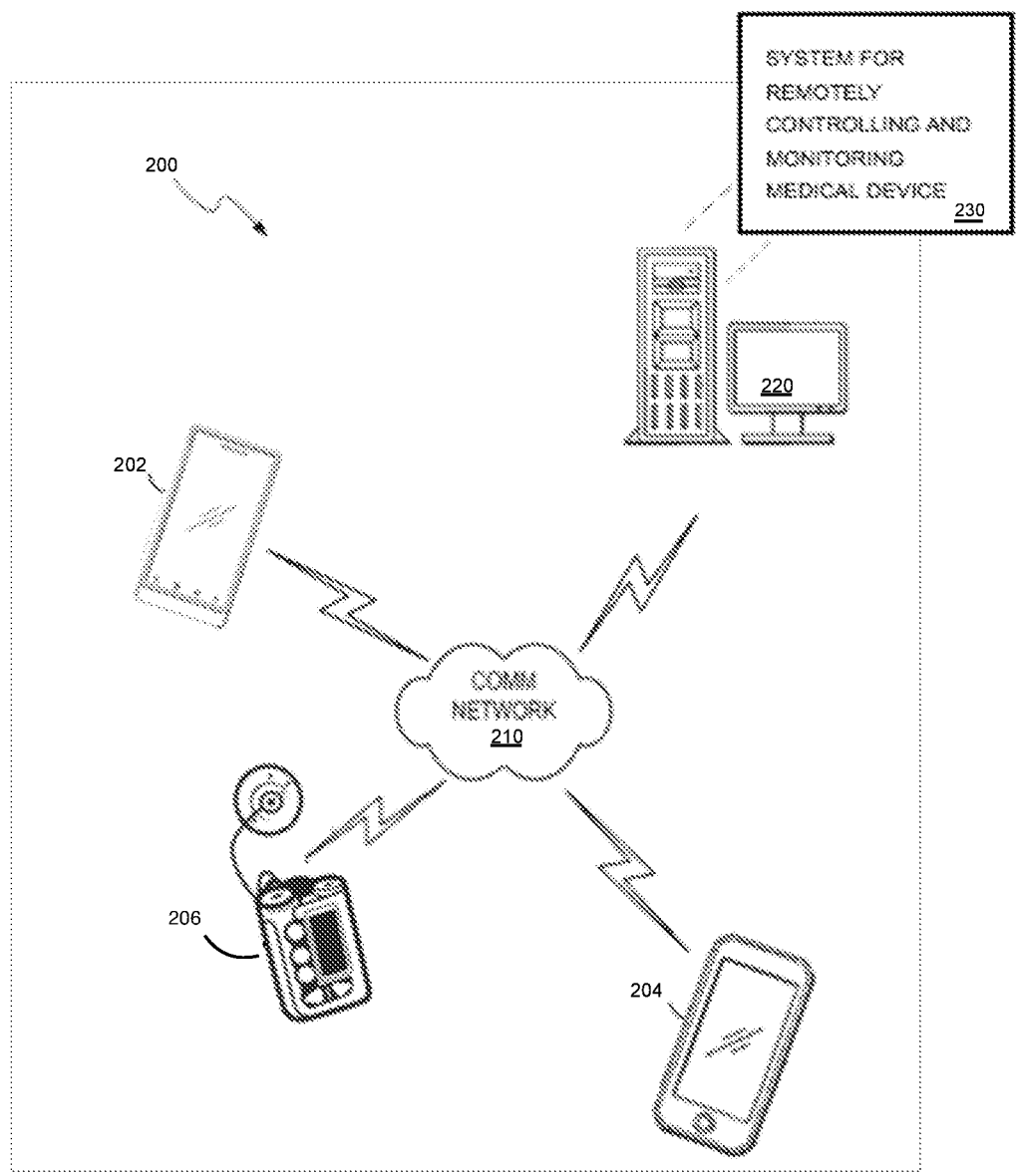
FIG. 2 illustrates an exemplary embodiment of a mobile device shown in FIG. 1 operative to remotely communicate with a medical device.

FIG. 2 illustrates an alternative networked environment in which another exemplary embodiment of a system for controlling and monitoring an electronic device is implemented. As shown in FIG. 2, system 200 comprises by way of example, and not limitation, two electronic devices 202 and 204 and one electronic wearable medical device 206 communicatively coupled via a communication network 210. Each of the electronic devices 202 and 204 may be embodied as a mobile computing device such as, for example and without limitation, a smartphone that incorporates cellular telephone functionality. Notably, the communications network can use one or more of various communications types such as, for example and without limitation, cellular and Wi-Fi communications.

Users of mobile devices 202 and 204 may use their devices to become members of a treatment network that enables them to interact with the patient, and in some embodiments, each other using their mobile devices 202 and 204 to remotely exchange information relating to patient's condition and further enable remote treatment. In this exemplary embodiment, the treatment network is facilitated by a website that is hosted by treatment network server 420. As such, server 420 facilitates interaction among a limited group of members, as may be established by the members themselves. More particularly, the limited group of members may be chosen or managed or otherwise approved by the patient himself, owing of course to the sensitive nature medical diagnosis and treatment, as discussed with reference to the network in FIG. 1 above. For the purpose of the example presented in FIG. 2, the limited group of members includes the users of electronic devices 402 and 404.

Additionally, server 220 implements the system for controlling and monitoring an electronic device and facilitates sharing information related to treatments with the patient amongst members of the treatment network, as permitted by the patient and laws relating to patient confidentiality, where applicable. Specifically, the server 220 implements the steps outlined in FIG. 3.

Figure 3A:
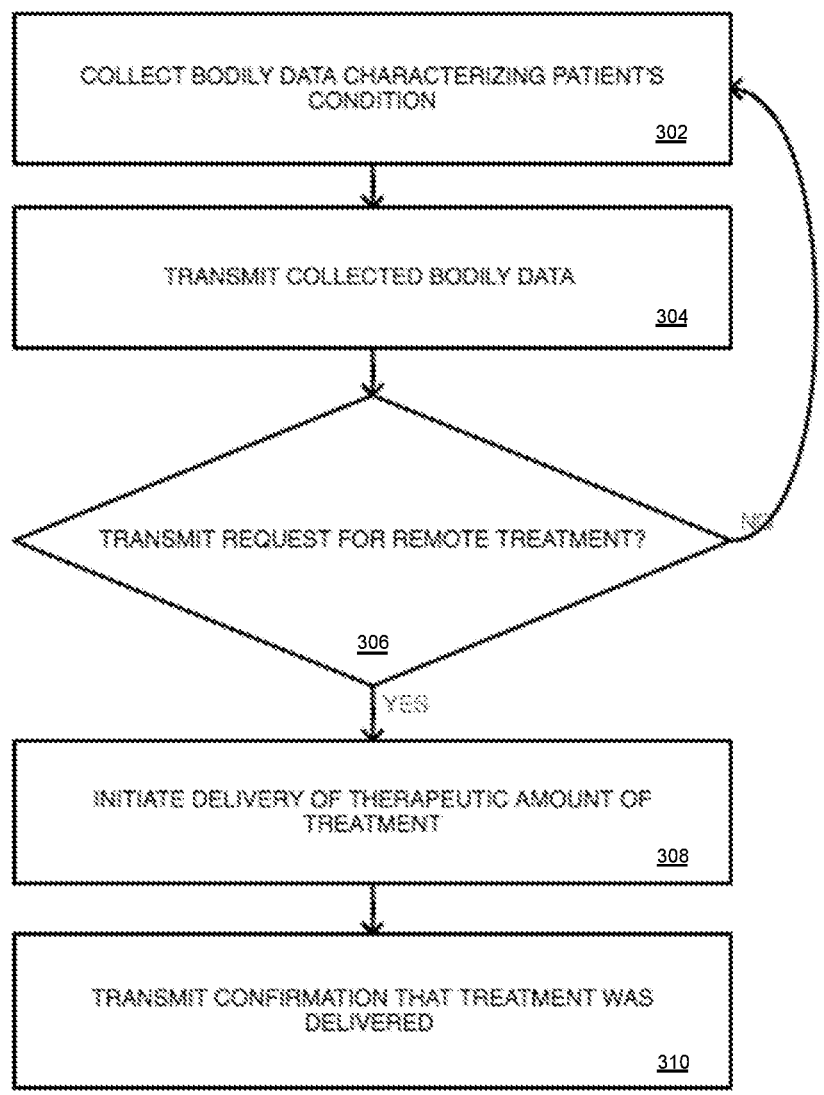
FIG. 3A is a flowchart depicting an exemplary embodiment of a method for remotely monitoring and controlling an electronic device as may be performed by the systems shown in FIGS. 1 and 2.
Figure 3B:
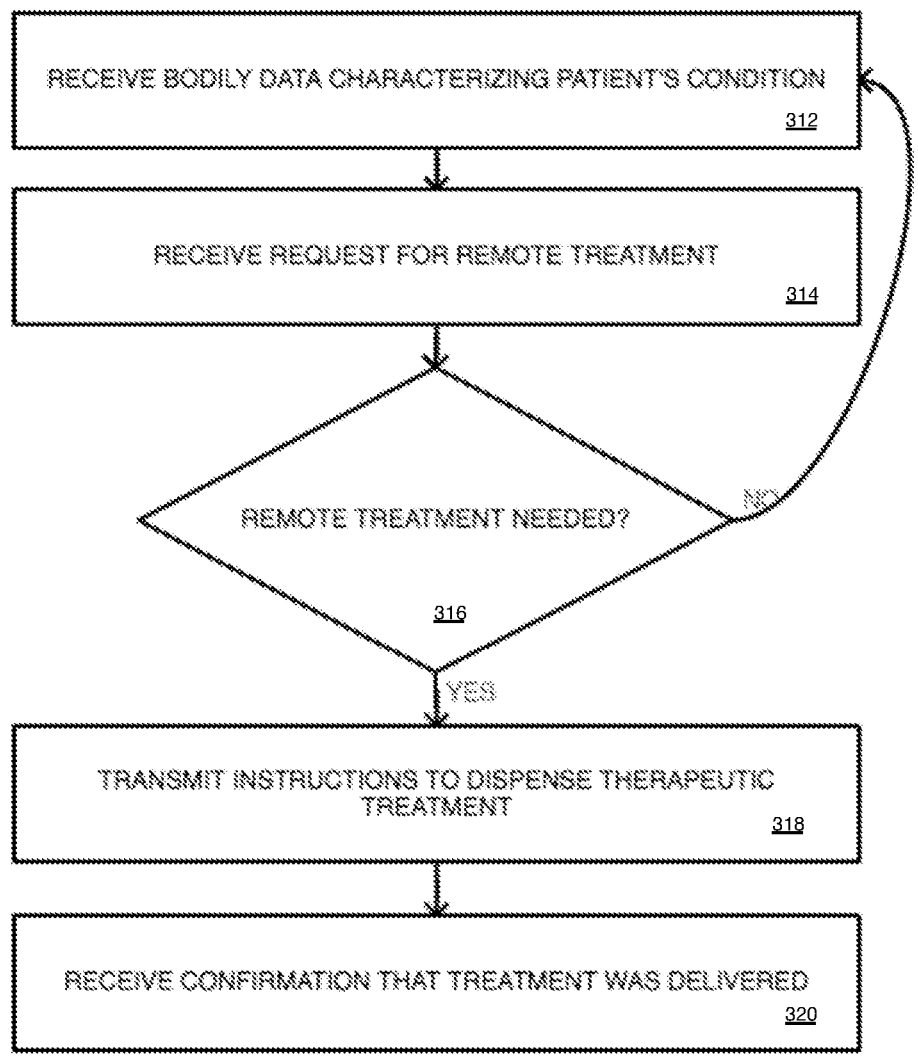
FIG. 3B is another flowchart depicting an exemplary embodiment of a method for remotely monitoring and controlling an electronic device as may be performed by the systems shown in FIGS. 1 and 2.

In particular, FIGS. 3A and 3B are flowcharts depicting an exemplary embodiment of a system and method for invention such as may be performed by electronic devices 202 and 204, and medical device 206 of FIG. 2. As shown in FIG. 3A, the method includes the steps of, at the medical device 106: collecting bodily data characterizing the patient's condition (block 302); transmitting the collected bodily data (block 304); and transmitting a request for remote treatment (block 306). It should be noted here that a request for remote treatment may occur automatically. This may be desirable in the event that the medical device measures unsafe bodily data, as compared to predetermined threshold amounts. For instance, the medical device may determine that the patient's blood sugar may be dangerously high or low and thus automatically transmit a request for remote treatment to members of the treatment network. An affirmative request for treatment may also occur, however. For instance, a patient may note unusual physiological effects of a certain meal and use their medical device to transmit a request for remote treatment, triggering remote prophylactic treatment by a remote party member of the treatment network. In the event that a request for remote treatment is transmitted (block 306), the method may further include, at the medical device: initiating delivery of therapeutic treatment (block 308) to the patient; and transmitting confirmation that treatment was delivered (block 310).

As shown in FIG. 3B, the method includes the steps of, at an electronic device in possession of a member of the treatment network remote from the patient: receive bodily data characterizing the patient's condition (block 312); receive a request for treatment (block 314); enabling a determination that remote treatment is needed (block 316); transmitting instructions to the medical device to dispense therapeutic prescription (block 318); and receive confirmation that treatment was delivered (block 320).

The steps of FIGS. 3A and 3B may be similarly performed by electronic devices 102 and 104, and medical device 106 of FIG. 1.

Accordingly, returning to FIG. 2, a member of the treatment network can access the server 220 using their electronic devices 202 and 204 to review any received bodily data and determine whether to transmit remote instructions to dispense treatment, or use their medical device 406 to collect and transmit bodily data and request remote treatment, as the case may be.

In order to facilitate the aforementioned functionality, various aspects may be performed by one or more of the electronic devices 202, 204 or the medical device 206. In one embodiment, the electronic devices 202, 204 and/or medical devices 206 are operative to perform, at least in part, the method depicted in the flowchart of FIG. 3, discussed above.

With respect to operation of system for controlling and monitoring an electronic device, system 430 may also or alternatively be operative to perform, at least in part, the method depicted in the flowchart of FIG. 3.

If embodied in software, it should be noted that each block depicted in the accompanying flowcharts represents a module, segment, or portion of code that comprises program instructions stored on a non-transitory computer readable medium to implement the specified logical function(s). In this regard, the program instructions may be embodied in the form of source code that comprises statements written in a programming language or machine code that comprises numerical instructions recognizable by a suitable execution system such as the electronic device 102, 104, 402 and 404 and medical devices 106 and 206. The machine code may be converted from the source code, etc. If embodied in hardware, each block may represent a circuit or a number of interconnected circuits to implement the specified logical function(s). Additionally, although the flowcharts show specific orders of execution, it is to be understood that the orders of execution may differ.

Figure 4:
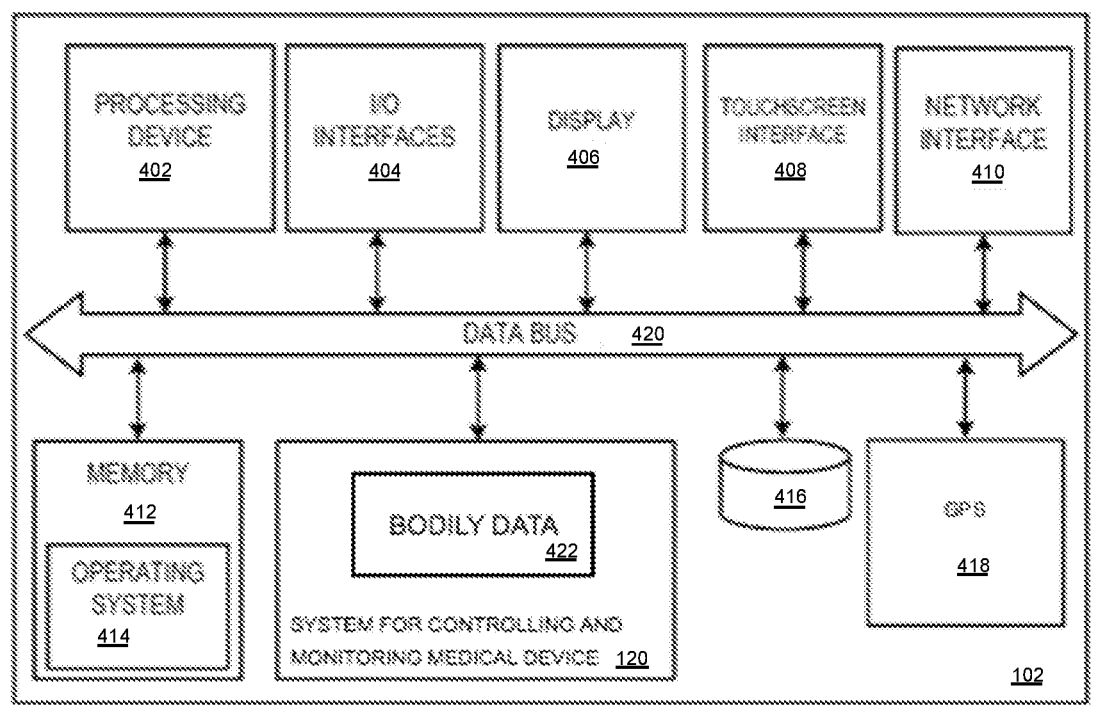
FIG. 4 illustrates an exemplary embodiment of an electronic device shown in FIG. 1.

FIG. 4 illustrates one embodiment electronic device 102 shown in FIG. 1. It is to be understood that such architecture may similarly, though not necessarily, define electronic device 104 and electronic devices 202 and 204 of FIG. 2. The foregoing is offered by way of example only, and not of limitation. One skilled in the art will recognize that a wide breadth of electronic devices, variously configured, may be used without departing from the invention.

As described earlier, the electronic device 102 may be a tablet, desktop, or laptop computer or smartphone but may also be embodied in any one of a wide variety of wired and/or wireless computing devices. As shown in FIG. 4, electronic device 102 includes a processing device (processor) 402, input/output interfaces 404, a display 406, a touchscreen interface 408, a network interface 410, a memory 412, and operating system 414, a mass storage 416 and an GPS 418, with each communicating across a local data bus 420. Additionally, electronic device 102 incorporates a system controlling and monitoring an electronic device 100, which is depicted as including bodily data 422, and perhaps even treatment history and other patient information, though the location of 422.

The processing device 402 may include any custom made or commercially available processor, a central processing unit (CPU) or an auxiliary processor among several processors associated with the electronic device 102, a semiconductor based microprocessor (in the form of a microchip), a macroprocessor, one or more application specific integrated circuits (ASICs), a plurality of suitably configured digital logic gates, and other electrical configurations comprising discrete elements both individually and in various combinations to coordinate the overall operation of the system.

The memory 412 can include any one of a combination of volatile memory elements (e.g., random-access memory (RAM, such as DRAM, and SRAM, etc.)) and nonvolatile memory elements. The memory typically comprises native operating system 414, one or more native applications, emulation systems, or emulated applications for any of a variety of operating systems and/or emulated hardware platforms, emulated operating systems, etc. For example, the applications may include application specific software which may comprise some or all the components of the mobile device 102. In accordance with such embodiments, the components are stored in memory and executed by the processing device. Note that although depicted separately in FIG. 4, the system and method for controlling and monitoring an electronic device 100 may be resident in memory such as memory 412.

Touchscreen interface 408 is configured to detect contact within the display area of the display 406 and provides such functionality as on-screen buttons, menus, keyboards, etc. that allows users to navigate user interfaces by touch. For some embodiments, the electronic device 102 will comprise GPS 418 or other means to determine the location of the electronic device 102.

One of ordinary skill in the art will appreciate that the memory 414 can, and typically will, comprise other components which have been omitted for purposes of brevity. Note that in the context of this disclosure, a non-transitory computer-readable medium stores one or more programs for use by or in connection with an instruction execution system, apparatus, or device. With further reference to FIG. 4, network interface device 310 comprises various components used to transmit and/or receive data over a networked environment such as depicted in FIG. 1. When such components are embodied as an application, the one or more components may be stored on a non-transitory computer-readable medium and executed by the processing device.

Figure 5:
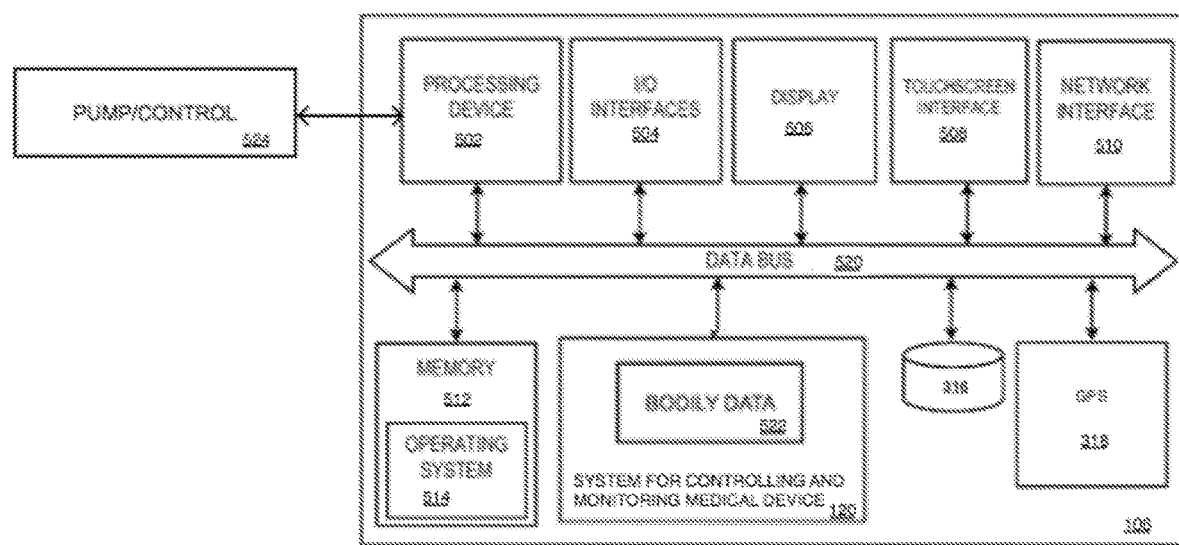
FIG. 5 illustrates an exemplary embodiment of a medical device shown in FIG. 1.

A block diagram illustrating an embodiment of the electronic wearable medical device, such as medical device 106 of FIG. 1, is also provided. With reference to FIG. 5 it may be seen that the medical device may comprise many of the same elements as the personal electronic device in FIG. 4. FIG. 5 includes, for example, a processing device (processor) 502, input/output interfaces 504, a display 506, a touchscreen interface 508, a network interface 510, a memory 512, and operating system 514, a mass storage 516 and an GPS 518, with each communicating across a local data bus 520 with the addition of pump or control 524 in communication with the processor. Said pump or control providing ultimate means for delivering therapeutic doses and prescriptions into the body of the patient.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

CONCLUSIONS, RAMIFICATIONS, AND SCOPE

While certain embodiments of the invention have been illustrated and described, various modifications are contemplated and can be made without departing from the spirit and scope of the invention. For example, the particular appearance of a user interface and any information accessible thereby should not be dispositive. A user interface may vary between remote parties depending a variety of factors such as, for example only and not limitation, the nature of the remote parties' respective relationship to the patient. Accordingly, it is intended that the invention not be limited, except as by the appended claim(s).

The teachings disclosed herein may be applied to other systems, and may not necessarily be limited to any described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions and concepts of the various references described above to provide yet further embodiments of the invention.

Particular terminology used when describing certain features or aspects of the invention should not be taken to imply that the terminology is being refined herein to be restricted to any specific characteristics, features, or aspects of the method, system, and apparatus for remotely controlling and monitoring an electronic device with which that terminology is associated. In general, the terms used in the following claims should not be constructed to limit the method, system, and apparatus for remotely controlling and monitoring an electronic device to the specific embodiments disclosed in the specification unless the above description section explicitly define such terms. Accordingly, the actual scope encompasses not only the disclosed embodiments, but also all equivalent ways of practicing or implementing the disclosed system, method and apparatus. The above description of embodiments of the method, system, and apparatus for remotely controlling and monitoring an electronic device is not intended to be exhaustive or limited to the precise form disclosed above or to a particular field of usage.

While specific embodiments of, and examples for, the method, system, and apparatus are described above for illustrative purposes, various equivalent modifications are possible for which those skilled in the relevant art will recognize.

While certain aspects of the method and system disclosed are presented below in particular claim forms, various aspects of the method, system, and apparatus are contemplated in any number of claim forms. Thus, the inventor reserves the right to add additional claims after filing the application to pursue such additional claim forms for other aspects of the method, system, and apparatus for remotely controlling and monitoring an electronic device.

What is claimed is:

1. A non-transitory, tangible computer-readable medium having stored thereon computer-executable instructions, which, when executed by a computer processor of an electronic wearable medical device of a patient of a private treatment network, the electronic wearable medical device comprising an infusion pump, enable performance of a method comprising:
   collecting bodily data characterizing a patient's condition at the electronic wearable medical device of the patient, wherein the collecting of the bodily data includes monitoring blood glucose levels of the patient over time;
   periodically transmitting, from the electronic wearable medical device, the bodily data characterizing the patient's condition to an electronic device controlled by a remote party of the private treatment network, the private treatment network comprising a communication network connecting the electronic wearable medical device of the patient and the electronic device controlled by the remote party;
   transmitting, from the electronic wearable medical device, a request for remote treatment of the patient to the electronic device controlled by the remote party, wherein the request is automatically generated by the computer processor responsive to determining that one of the monitored blood glucose levels of the patient falls below or exceeds an acceptable range of blood glucose levels for the patient from a predetermined threshold value;
   responsive to receipt of the request for remote treatment of the patient at the electronic device controlled by the remote party, receiving control instructions from the electronic device controlled by the remote party at the electronic wearable medical device to automatically start delivering one of glucose or insulin into the patient's body, or to automatically stop delivering one of glucose or insulin into the patient's body, depending on whether the monitored blood glucose level of the patient falls below or exceeds the acceptable range of blood glucose levels for the patient from the predetermined threshold value;
   controlling the infusion pump to start delivering one of glucose or insulin into the patient's body, or to stop delivering one of glucose or insulin into the patient's body, based on the control instructions received from the electronic device controlled by the remote party;
   transmitting, from the electronic wearable medical device, a confirmation to the electronic device controlled by the remote party that the starting of the delivering of one of glucose or insulin into the patient's body, or the stopping of the delivering of one of glucose or insulin into the patient's body, was performed successfully via the infusion pump responsive to receipt of the control instructions; and
   generating, by the electronic wearable medical device of the patient, a report characterizing the patient's bodily data over time.

2. The non-transitory, tangible computer-readable medium having stored thereon computer-executable instructions, which, when executed by the computer processor of the electronic wearable medical device, enable performance of the method of claim 1, further comprising:
   transmitting, from the wearable electronic medical device, a geographic location of the patient to the electronic device controlled by the remote party.

3. The non-transitory, tangible computer-readable medium having stored thereon computer-executable instructions, which, when executed by the computer processor of the electronic wearable medical device, enable performance of the method of claim 2, wherein:

the transmitting, from the wearable electronic medical device, of the geographic location of the patient to the electronic device controlled by the remote party occurs responsive to the determination that the monitored blood glucose level of the patient exceeds or falls below the acceptable range of blood glucose levels for the patient from the predetermined threshold amount.

4. The non-transitory, tangible computer-readable medium having stored thereon computer-executable instructions, which, when executed by the computer processor of the electronic wearable medical device, enable performance of the method of claim 1, further comprising:
   capturing ambient sound that is proximate to the patient via a microphone of the electronic wearable medical device of the patient, wherein the ambient sound includes sounds of the patient and a surrounding environment of the patient; and
   transmitting, from the wearable electronic medical device, the ambient sound proximate to the patient to the electronic device controlled by the remote party.

5. The non-transitory, tangible computer-readable medium having stored thereon computer-executable instructions, which, when executed by the computer processor of the electronic wearable medical device, enable performance of the method of claim 4, wherein:
   the transmitting, from the wearable electronic medical device, of the ambient sound proximate to the patient to the electronic device controlled by the remote party occurs responsive to the determination that the monitored blood glucose level of the patient exceeds or falls below the acceptable range of blood glucose levels of the patient from the predetermined threshold amount.

6. The non-transitory, tangible computer-readable medium having stored thereon computer-executable instructions, which, when executed by the computer processor of the electronic wearable medical device, enable performance of the method of claim 1, further comprising:
   receiving control instructions from the electronic device controlled by the remote party to adjust a dosage or timing of delivering glucose or insulin into the patient's body based on the collected bodily data characterizing the patient's condition;
   controlling the infusion pump to adjust the dosage or timing of the delivering of one of glucose or insulin into the patient's body based on the control instructions received from the electronic device controlled by the remote party; and
   transmitting, from the electronic wearable medical device, a confirmation to the electronic device controlled by the remote party that the adjusting of the dosage or timing of the delivering of one of glucose or insulin into the patient's body was performed successfully via the infusion pump responsive to receipt of the control instructions.

7. A non-transitory, tangible computer-readable medium having stored thereon computer-executable instructions, which, when executed by a computer processor of an electronic device controlled by a remote party of a private treatment network, enable performance of a method comprising:
   periodically receiving, at the electronic device controlled by the remote party, bodily data characterizing a patient's condition from an electronic wearable medical device of a patient of the private treatment network, the bodily data including monitored blood glucose levels of the patient over time, and the private treatment network comprising a communication network connecting the electronic device controlled by the remote party and the electronic wearable medical device of the patient;
   receiving, at the electronic device controlled by the remote party, a request for remote treatment of the patient from the electronic wearable medical device of the patient, wherein the request indicates that one of the monitored blood glucose levels of the patient falls below or exceeds an acceptable range of blood glucose levels for the patient from a predetermined threshold value, as measured by the electronic wearable medical device of the patient;
   transmitting, from the electronic device controlled by the remote party, control instructions to the electronic wearable medical device of the patient to control an infusion pump included in the electronic wearable medical device to automatically start delivering one of glucose or insulin into the patient's body, or to automatically stop delivering one of glucose or insulin into the patient's body, depending on whether the monitored blood glucose level of the patient falls below or exceeds the acceptable range of blood glucose levels for the patient from the predetermined threshold value;
   responsive to receipt of the control instructions at the electronic wearable medical device of the patient, receiving confirmation from the electronic wearable medical device of the patient at the electronic device controlled by the remote party that the starting of the delivering of one of glucose or insulin into the patient's body, or the stopping of the delivering of one of glucose or insulin into the patient's body, was performed successfully via the infusion pump based on the control instructions; and
   generating, by the electronic device controlled by the remote party, a report characterizing the patient's bodily data over time.

8. The non-transitory, tangible computer-readable medium having stored thereon computer-executable instructions, which, when executed by the computer processor of the electronic device controlled by the remote party, enable performance of the method of claim 7, further comprising:
   receiving, at the electronic device controlled by the remote party, a geographic location of the patient from the electronic wearable medical device of the patient.

9. The non-transitory, tangible computer-readable medium having stored thereon computer-executable instructions, which, when executed by the computer processor of the electronic device controlled by the remote party, enable performance of the method of claim 8, wherein:
   the receiving, at the electronic device controlled by the remote party, of the geographic location of the patient from the electronic wearable medical device of the patient occurs responsive to a determination that the monitored blood glucose level of the patient exceeds or falls below the acceptable range of blood glucose levels from the predetermined threshold value, as measured by the electronic wearable medical device.

10. The non-transitory, tangible computer-readable medium having stored thereon computer-executable instructions, which, when executed by the computer processor of the electronic device controlled by the remote party, enable performance of the method of claim 7, further comprising:
    receiving, at the electronic device controlled by the remote party, ambient sound that is proximate to the patient from the electronic wearable medical device of the patient, wherein the ambient sound proximate to the patient is captured via a microphone of the electronic wearable medical device and includes sounds of the patient and a surrounding environment of the patient.

11. The non-transitory, tangible computer-readable medium having stored thereon computer-executable instructions, which, when executed by the computer processor of the electronic device controlled by the remote party, enable performance of the method of claim 10, wherein:

the receiving, at the electronic device controlled by the remote party, of the ambient sound proximate to the patient occurs responsive to a determination that the monitored blood glucose level of the patient exceeds or falls below the acceptable range of blood glucose levels for the patient from the predetermined threshold amount, as measured by the electronic wearable medical device.

12. The non-transitory, tangible computer-readable medium having stored thereon computer-executable instructions, which, when executed by the computer processor of the electronic device controlled by the remote party, enable performance of the method of claim 7, further comprising:

transmitting, from the electronic device controlled by the remote party, control instructions to the electronic wearable medical device of the patient to control the infusion pump to adjust a dosage or timing of delivering glucose or insulin into the patient's body based on the bodily data characterizing the patient's condition; and receiving confirmation from the electronic wearable medical device of the patient at the electronic device controlled by the remote party that the adjusting of the dosage or timing of the delivering of glucose or insulin into the patient's body was performed successfully via the infusion pump based on the control instructions.

* * * * *